(12) United States Patent
Sinay et al.

(10) Patent No.: US 10,646,104 B1
(45) Date of Patent: May 12, 2020

(54) DISPOSABLE ENDOSCOPE

(71) Applicant: G.I. View Ltd., Ramat Gan (IL)

(72) Inventors: Avraham Sinay, Petach-Tikva (IL); Yuval Raz, Modiin (IL); Zohar Deli, Ramat Bet Shemesh (IL); Ziv Rozenker, Ramat-Gan (IL); Albert Sviridovski, Petah-Tikva (IL)

(73) Assignee: G.I. VIEW LTD., Ramat Gan (IL)

( * ) Notice: Subject to any disclaimer, the term of this patent is extended or adjusted under 35 U.S.C. 154(b) by 0 days.

(21) Appl. No.: 16/453,613

(22) Filed: Jun. 26, 2019

Related U.S. Application Data

(60) Provisional application No. 62/752,009, filed on Oct. 29, 2018.

(51) Int. Cl.
| | |
|---|---|
| *A61B 1/00* | (2006.01) |
| *A61B 1/005* | (2006.01) |
| *A61M 16/04* | (2006.01) |
| *A61B 17/00* | (2006.01) |
| *A61B 1/01* | (2006.01) |
| *A61B 1/04* | (2006.01) |

(52) U.S. Cl.
CPC ........ *A61B 1/00147* (2013.01); *A61B 1/0057* (2013.01); *A61B 1/00066* (2013.01); *A61B 1/00103* (2013.01); *A61B 1/01* (2013.01); *A61B 1/04* (2013.01); *A61B 2017/0023* (2013.01); *A61M 16/0418* (2014.02)

(58) Field of Classification Search
USPC ........................................................ 600/137
See application file for complete search history.

(56) References Cited

U.S. PATENT DOCUMENTS

| | | |
|---|---|---|
| 3,998,216 A | 12/1976 | Hosono |
| 4,432,349 A | 2/1984 | Oshiro |
| 4,686,963 A | 8/1987 | Cohen et al. |
| 4,700,693 A | 10/1987 | Lia et al. |
| 4,748,969 A | 6/1988 | Wardle |
| 4,770,188 A | 9/1988 | Chikama |

(Continued)

FOREIGN PATENT DOCUMENTS

| | | |
|---|---|---|
| CN | 102789050 A | 11/2012 |
| CN | 102469917 B | 12/2014 |

(Continued)

OTHER PUBLICATIONS

ECRI Institute, "Top 10 Health Technology Hazards for 2011", Reprinted from vol. 39 Issue 11, Nov. 2010, 16 pages.

(Continued)

*Primary Examiner* — John P Leubecker
*Assistant Examiner* — Shankar Raj Ghimire
(74) *Attorney, Agent, or Firm* — Dorsey & Whitney LLP

(57) ABSTRACT

The present invention relates to an intubation system comprising insertion unit to be connected to a bending section of a medical instrument comprising an inner elongated shaft structure being capable of torque transmission around its length axis and an outer elongated shaft structure surrounding the inner elongated shaft structure and having a continuous outer surface, and an orientation controller being attached to the inner elongated shaft, such that when the orientation controller rotates, the bending section turns around itself.

6 Claims, 6 Drawing Sheets
(6 of 6 Drawing Sheet(s) Filed in Color)

(56) References Cited

U.S. PATENT DOCUMENTS

| | | |
|---|---|---|
| 4,826,087 A | 5/1989 | Chinery |
| 4,911,148 A | 3/1990 | Sosnowski et al. |
| 5,005,558 A | 4/1991 | Aomori |
| 5,137,013 A | 8/1992 | Chiba et al. |
| 5,174,276 A | 12/1992 | Crockard |
| 5,174,277 A | 12/1992 | Matsumaru |
| 5,179,935 A | 1/1993 | Miyagi |
| 5,325,845 A | 7/1994 | Adair |
| 5,381,782 A | 1/1995 | Delarama et al. |
| 5,520,222 A | 5/1996 | Chikama |
| 5,601,537 A | 2/1997 | Frassica |
| 5,679,216 A | 10/1997 | Takayama et al. |
| 5,873,817 A | 2/1999 | Kokish et al. |
| 5,899,914 A | 5/1999 | Zirps et al. |
| 6,013,024 A | 1/2000 | Mitsuda et al. |
| 6,270,453 B1 | 8/2001 | Sakai |
| 6,364,828 B1 | 4/2002 | Yeung et al. |
| 6,875,170 B2 | 4/2005 | Francois et al. |
| 7,052,489 B2 | 5/2006 | Griego et al. |
| 7,147,650 B2 | 12/2006 | Lee |
| 7,591,783 B2 | 9/2009 | Boulais et al. |
| 7,637,905 B2 | 12/2009 | Saadat et al. |
| 8,257,249 B2 * | 9/2012 | Sugisawa ............ A61B 1/00071 600/128 |
| 8,500,628 B2 * | 8/2013 | Frassica ............. A61B 1/00082 600/114 |
| 8,512,228 B2 | 8/2013 | Vargas |
| 8,550,989 B2 | 10/2013 | Dohi et al. |
| 8,702,594 B2 * | 4/2014 | Edidin ............... H01R 13/6205 439/38 |
| 9,155,451 B2 | 10/2015 | Smith et al. |
| 9,636,481 B2 * | 5/2017 | Campbell ......... A61M 25/0136 |
| 9,907,456 B2 * | 3/2018 | Miyoshi ............... A61B 1/0016 |
| 2002/0017515 A1 | 2/2002 | Obata et al. |
| 2002/0133077 A1 * | 9/2002 | Edwardsen ........ A61B 1/00177 600/462 |
| 2003/0176849 A1 | 9/2003 | Wendlandt et al. |
| 2004/0138525 A1 | 7/2004 | Saadat et al. |
| 2004/0199052 A1 | 10/2004 | Banik et al. |
| 2004/0242966 A1 | 12/2004 | Barry et al. |
| 2005/0065397 A1 | 3/2005 | Saadat et al. |
| 2005/0154278 A1 * | 7/2005 | Cabiri ................ A61B 1/00156 600/407 |
| 2005/0272976 A1 * | 12/2005 | Tanaka ............... A61B 1/00073 600/114 |
| 2006/0146127 A1 | 7/2006 | Bagley et al. |
| 2007/0004967 A1 * | 1/2007 | Ueno .................. A61B 1/0052 600/152 |
| 2007/0232858 A1 | 10/2007 | Macnamara et al. |
| 2007/0276430 A1 | 11/2007 | Lee et al. |
| 2007/0282371 A1 * | 12/2007 | Lee ..................... A61B 17/062 606/205 |
| 2008/0065116 A1 | 3/2008 | Lee et al. |
| 2009/0171159 A1 | 7/2009 | Dennis et al. |
| 2009/0182268 A1 | 7/2009 | Thielen et al. |
| 2009/0234186 A1 | 9/2009 | Lin et al. |
| 2009/0240110 A1 | 9/2009 | Miyawaki et al. |
| 2009/0299344 A1 | 12/2009 | Lee et al. |
| 2010/0298642 A1 | 11/2010 | Trusty et al. |
| 2010/0324370 A1 | 12/2010 | Dohi et al. |
| 2011/0238108 A1 | 9/2011 | Peine et al. |
| 2011/0288374 A1 | 11/2011 | Hadani et al. |
| 2012/0029281 A1 * | 2/2012 | Frassica ............ A61B 1/00082 600/114 |
| 2012/0053607 A1 | 3/2012 | Adams |
| 2012/0199632 A1 * | 8/2012 | Spivey ............ A61B 17/07207 227/176.1 |
| 2012/0277671 A1 | 11/2012 | Fuentes |
| 2013/0041222 A1 * | 2/2013 | Moriyama ......... A61B 1/00073 600/114 |
| 2013/0096384 A1 * | 4/2013 | Arai .................... A61B 1/0055 600/144 |
| 2015/0066033 A1 | 3/2015 | Jorgensen |
| 2015/0080649 A1 | 3/2015 | Ayrenschmalz et al. |
| 2016/0296105 A1 | 10/2016 | Ramsey |
| 2017/0071447 A1 * | 3/2017 | Nishiie .............. A61B 1/00071 |
| 2017/0202570 A1 * | 7/2017 | Shelton, IV ....... A61B 18/1447 |
| 2018/0049625 A1 * | 2/2018 | Nakade .............. A61B 1/00071 |
| 2018/0110506 A1 * | 4/2018 | Thommen ............ A61B 17/025 |
| 2019/0059923 A1 * | 2/2019 | Tillman ............. A61B 17/2909 |
| 2019/0209154 A1 * | 7/2019 | Richter .............. A61B 1/00045 |
| 2019/0261984 A1 * | 8/2019 | Nelson ............. A61B 17/07207 |

FOREIGN PATENT DOCUMENTS

| | | |
|---|---|---|
| CN | 102596064 B | 2/2015 |
| EP | 1017323 A1 | 7/2000 |
| EP | 2248483 A4 | 3/2014 |
| EP | 3184026 A1 | 6/2017 |
| JP | 2573602 B2 | 7/1993 |
| JP | H06343702 A | 12/1994 |
| JP | 2011083549 A | 4/2011 |
| WO | 2009107792 A1 | 9/2009 |

OTHER PUBLICATIONS

Spach, David H. et al., "Transmission of Infection by Gastrointestinal Endoscopy and Bronchoscopy", Annals of Internal Medicine vol. 118, No. 2, Jan. 15, 1993, pp. 117-128.

* cited by examiner

DISPOSABLE ENDOSCOPE

FIELD OF THE INVENTION

The present invention relates generally to the field of medical instruments, and more specifically, to disposable endoscopes.

BACKGROUND OF THE INVENTION

An endoscope is an instrument used to see inside a body lumen. A conventional medical endoscope includes a flexible tube, a functional control mechanism to direct the position of a distal end of the flexible tube, and a camera. The camera provides images of the internal body cavity to help the medical practitioner position the distal end of the flexible tube and confirm that the end is positioned at an acceptable location. When the endoscope is used in a medical procedure, the flexible tube of an endoscope is generally directed into an internal body cavity of a patient. During its use in the procedure by a medical practitioner, the endoscope may acquire high levels of microbial contamination. Such microbial contamination may include infectious agents or any number of harmful bacterial and viral microorganisms. In some cases, an endoscope used in a medical procedure on one patient is contaminated, improperly or insufficiently disinfected, and is then used in a medical procedure on another patient. In such cases, the health of the second patient is put at risk of microbial transmission or disease.

Medical practitioners work to prevent the spread of infection and disease by following strict procedures to clean and disinfect an endoscope. Unfortunately, most conventional endoscopes (e.g., bronchoscopes, colonoscopes, gastrointestinal endoscopes, nasopharyngoscopes, sigmoidoscopes, and the like) are heat sensitive and cannot be sterilized. Instead, the endoscopes are cleaned using alternative procedures, and are wiped, or even bathed, in high-level disinfectants.

When endoscopes are made of materials that can be sterilized, the hospital needs to set up a dedicated sterilization chamber and equip it with dedicated sterilization equipment and corresponding operators. The required sterilization procedure limits the frequency of reuse, and still carries the risk of cross infection etc. caused by imperfect sterilization.

In spite of rigid attempts to effectively clean endoscopes, some patients suffer injury, illness, and even death as a result of an endoscope that carries pathogens from one patient to another. In 2010, the ECRI Institute cited endoscopic contamination as one of the top 10 health risks in a document entitled "Top 10 Health Technology Hazards for 2011," Reprinted from Volume 39, Issue 11, November 2012 by the ECRI Institute (www.ecri.org). A seminal work that studied and described the problem of improperly cleaned endoscopes is "Transmission of Infection by Gastrointestinal Endoscopy and Bronchoscopy," from the Annals of Internal Medicine, 1993; 118:117-128 by the American College of Physicians.

Flexible endoscopes in general, and colonoscopes in particular, are difficult to clean and disinfect thoroughly, leading to potential problems of cross-contamination between patients, and between patients and staff. Additionally, such endoscopes often use costly devices such as camera heads, electro-mechanical steering devices, and control electronics modules, which cannot be readily sterilized, and because of their cost, cannot be discarded after every use.

The Centers for Disease Control and Prevention (CDC) and U.S. Food and Drug Administration (FDA) are alerting healthcare providers and facilities about the public health need to properly maintain, clean, and disinfect or sterilize reusable medical devices. Infection control lapses due to non-compliance with recommended reprocessing procedures highlight a critical gap in patient safety. Healthcare facilities (e.g., hospitals, ambulatory surgical centers, clinics, and doctors' offices) that utilize reusable medical devices are urged to review reprocessing practices at their facility to ensure they are complying with all steps as directed by the device manufacturers, and have in place appropriate policies and procedures that are consistent with standards and guidelines. Safety communications are published every year to guide hospitals and health care facilities that utilize colonoscopes to take additional steps to further reduce the risk of infection and increase the safety of these medical devices. They recognize that not all health care facilities can implement one or more of these measures, which require specific resources, training, and expertise. Reprocessing instructions are provided as a detailed, multistep process to clean and disinfect or sterilize reusable devices, and can result in infection transmission if reprocessing instructions are not followed in every step of the process.

GENERAL DESCRIPTION

According to a broad aspect of the present invention, there is provided an intubation system comprising (a) insertion unit to be connected to a bending section of a medical instrument comprising an inner elongated shaft structure being capable of torque transmission around its length axis and an outer elongated shaft structure surrounding the inner elongated shaft structure and having a continuous outer surface, and (b) an orientation controller being attached to the inner elongated shaft, such that when the orientation controller rotates, the bending section turns around itself. The orientation controller is configured and operable to transmit torsion forces from an operator's hand to the distal end such that rotation of the orientation controller rotates the inner elongated shaft structure inside the outer elongated shaft structure and thereby rotates a distal end of the insertion system around itself without changing the outer elongated shaft structure's position inside the body lumen.

The orientation controller may be an integral part of an endoscopic system (e.g. comprising an image capturing device which is steered to any desired destination to enable to image a body lumen and perform polypectomy), or may be coupled to elements forming together an endoscope. The insertion unit refers hereinafter to the part of an endoscope device connecting between an orientation controller being configured to transmit forces from the operator's hand to the bending section of the intubation system and the optical head of the endoscope. The orientation controller of the present invention may be thus connected to any commercially available insertion unit.

According to another broad aspect of the present invention there is provided an orientation controller to be connected to an insertion unit of an endoscopic device having a rotatable bending section. The orientation controller comprises a handle to be handled by an operator, a rotatable bearing structure connecting between the handle and the insertion unit and being configured and operable to rotate the rotatable bending section of the insertion unit and a mode selector capable having a locked mode and an unlocked mode, wherein operation of the locked mode allowing the operator to rotate the rotatable bending section by rotating the handle, and operation of the unlocked mode allowing the operator to rotate the rotatable bending section by rotating the rotatable bearing structure.

The present invention thus provides a manually operable mechanical structure (i.e. an orientation controller) being capable of rotating a bending section of an endoscopic device being located within a body lumen. This special configuration enables to transfer a torque from an operator's hand to a bending section of an insertion unit by (1) rotating the handle of the orientation controller being attached to an insertion unit via a rotatable bearing structure, while the rotatable bearing structure is locked or (2) rotating the rotatable bearing structure, while the rotatable bearing structure is unlocked. Therefore, in the locked mode, the rotatable bearing structure is blocked such that the elongated shaft structure itself rotates, forming together a rigid unit such that any rotation of the handle rotates the distal tip/bending section. In other words, in the locked mode, the mode selector is configured to block the rotatable bearing structure to rotate the bending section by rotating the handle together with the rotatable bearing structure and in the unlocked mode in which the rotation is made by rotating the rotatable bearing structure, the mode selector is configured to release the rotatable bearing structure.

A second way is transferring the torque by rotating the rotatable bearing structure only, while the rotatable bearing structure is unlocked. Therefore, the unlocked mode disconnects the handle from the rotatable bearing structure and enables the rotatable bearing structure that is fixed to the inner elongated shaft structure and to the outer elongated structure, to be free for rotating and transferring the torque directly to the distal tip by itself through the inner elongated shaft structure.

In some embodiments, the insertion unit comprises an inner elongated shaft structure and outer elongated shaft structure, wherein the outer elongated shaft structure surrounds the inner elongated shaft structure. In this case, in the unlocked mode, the rotatable bearing structure is free to rotate, such that the inner elongated shaft structure itself rotates within the outer elongated shaft structure without affecting the position of the insertion unit. In the locked mode, the inner shaft bearing is connected to the orientation structure and is free to rotate the optical head.

In some embodiments, the rotatable bearing structure comprises an inner rotatable bearing element being configured for connecting between the inner elongated shaft structure and the handle and an outer rotatable bearing element connected to the outer elongated shaft structure such the rotatable bearing structure is configured for allowing the inner elongated shaft to rotate inside the outer elongated shaft of the insertion unit.

In some embodiments, the rotatable bearing structure comprises a gear mechanism having an outer wheel configured to block rotation of rotatable bearing structure upon operation of the mode selector and an inner wheel configured to being capable of free rotation by the outer wheel and to hold an extremity of the rotatable bending section. The gear mechanism may be configured to allow free rotation between the outer elongated shaft structure and the inner elongated shaft structure. The gear mechanism may further comprise an outer shaft holder configured to hold an extremity of the outer elongated shaft structure, wherein the inner wheel is configured to hold an extremity of the inner elongated shaft structure.

According to another broad aspect, the present invention provides a novel disposable endoscope having disposable components eliminating the need to sterilize the medical instrument. This requirement involves the use of low-cost material. To fulfill the requirements of mass production techniques, the steering mechanism might be made of injected plastic parts (e.g. injection molded). Moreover, to appropriately steer the device at any desired angle and position, the steerable portion of the tube should be flexible and the steering threads should have the following physical properties: withstanding a high load (e.g. about 20 kg), high abrasion resistance, high suppleness, high flexibility and low spool memory. Steel cables, usually used in steering devices, do not have these required properties. Therefore, there is provided an endoscope comprising a steering mechanism having at least two steering threads are made of a non-metal material. The steering threads of the present invention may thus be selected to be a thread made of polymer material, such as plastic. For example, steering threads are configured as braided fishing line. The braided line may be made of any one of copolymer, fluorocarbon, and nylon-based monofilaments. However, due to their lack of stretch and slippery surface, threads made of plastic are hard to knot properly. Fastening a non-metal steering thread to a pulley, while withstanding high forces and elongation, is a challenging task. To this end, the present invention provides a novel thread pulling device having a special configuration being aimed at properly holding steering threads being made of non-metal material having the physical properties as defined above.

The steering mechanism is configured for one-handed, either-handed use. The bending section is torque stable, rotatable and steerable. The handle of the endoscopic device (i.e. orientation controller) and the insertion unit are configured for use on a single patient and are disposed of after use in a single medical procedure.

In some embodiments, at least two steering threads are made of a non-metal material.

In some embodiments, the endoscope further comprises a thread pulling device configured and operable for fastening at least two non-metal steering threads. The thread pulling device includes at least one pulley on which the at least two steering threads are enwrapped. A first pulley may be configured and operable for directing the distal end portion leftwards and rightwards, and a second pulley may be configured and operable for directing the distal end portion downwards and upwards. The pulleys are connected to each other and are operated independently.

In some embodiments, the thread pulling device further comprises a locking mechanism configured and operable to lock the steering mechanism in a locked steered position.

According to another broad aspect of the present invention, there is provided an endoscope comprising a gas release valve configured to control the level of pressure exiting from a gas supply by releasing gas to the environment when the pressure reaches a certain threshold.

BRIEF DESCRIPTION OF THE FIGURES

The patent or application file contains at least one drawing executed in color. Copies of this patent or patent application publication with color drawing(s) will be provided by the Office upon request and payment of the necessary fee.

In order to understand the invention and to see how it may be implemented in practice, preferred embodiments will now be described, by way of non-limiting example only, with reference to the accompanying drawing, in which FIG. 1 schematically illustrates an example of an endoscopic device incorporating an orientation controller according to some embodiments of the present invention.

DETAILED DESCRIPTION OF EMBODIMENTS

Figure 1:
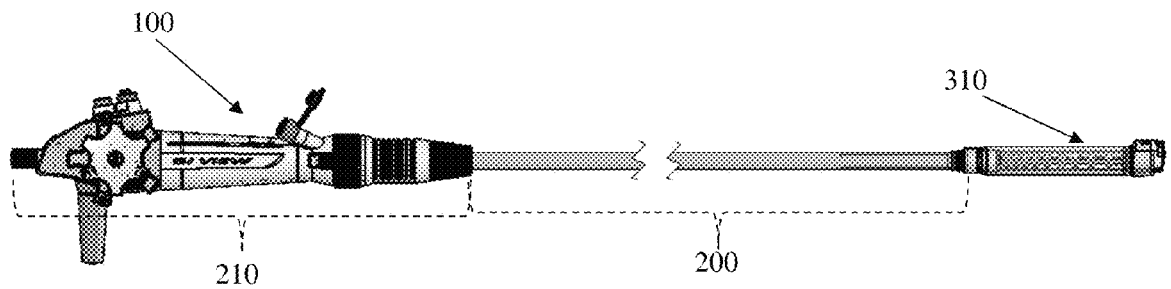

Performing colonoscopy or even polypectomy procedures requires a great deal of skill from the operator to manipulate the distal tip to a desirable position and use a therapeutic tool to perform the procedure. Reference is made to FIG. 1, illustrating an example of an endoscopic device 100 incorporating an operator's orientation controller 210 of the present invention. The present invention provides a novel configuration of an orientation controller 210 to be connected to an insertion unit 200 for performing safe procedures. The insertion unit 200 is configured for guiding an endoscope through a body lumen with low danger for the patient. Navigation of a distal tip is possible by using both deflection of a bending section 310 of the endoscopic device 100 (e.g. using knobs or a joystick) together with rotation of the bending section 310 and even of the insertion unit 200 if desired. The novel insertion unit 200 allows the operator to rotate the bending section 310 from operator's orientation controller 210, without rotating the insertion unit 200 if desired. The insertion unit 200 may be also rotated as will be described further below. Insertion unit 200 connects between an orientation controller 210 (e.g. a grip comprising valves, steering knobs and buttons) located in the handle to the bending section 310 including an optical head. Insertion unit 200 has the capability to advance through a tortuous body lumen fitting the looped configuration of the body lumen shape, transmitting pushing, rotation and bending forces from one extremity to the other, despite the possible looped condition of the shaft. The physical properties required for the insertion unit 200 are appropriate flexibility and restoring performance against bending, pushability and torque transmission performance (generically called "operationality") for transmitting an operational force from the proximal end portion to the distal side, and kink resistance (often called "resistance against sharp bending"). Insertion unit 200 is connected to the bending section 310.

Figure 2A:
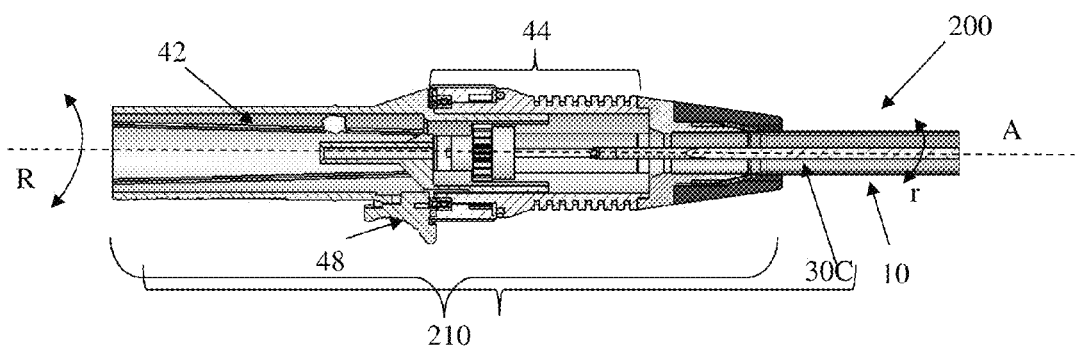
FIG. 2A schematically illustrates a partial view of an example of an orientation controller according to some embodiments of the present invention.

Reference is made to FIG. 2A illustrating an example of the configuration of an orientation controller 210, according to some embodiments of the present invention. The orientation controller 210 is configured to be connected to an insertion unit 200 of an endoscopic device having a rotatable and steering bending section. The insertion unit may be formed of a unit made of an elongated shaft as illustrated in FIG. 1. In some embodiments, the inner elongated shaft structure may be implemented by an elongated torsion shaft 30C surrounded by the outer hollow elongated shaft structure 10. In this context, in the specification and in the claims, "torsion shaft" refers to a rotatable flexible non-hollow cable having a non-continuous surface driven by gearing linked to the output of the orientation controller 210. The non-continuous property of the inner elongated shaft structure enables to transmit pushing and rotation forces along the length of the insertion tube 200. When the operator turns orientation controller 210 in both rotational directions R, orientation controller 210 turns the torsion shaft 30C in both rotational directions r. This shaft can transfer a great amount of torsion and remain very flexible. In this connection, it should be understood that since torsion shaft 30C is not hollow, a plurality of channels may be accommodated between the outer structure 10 and the torsion shaft 30C as will be illustrated further below. Moreover, torsion shaft 30C is capable of transmitting torque even if it is wrapped around itself, because of the loops naturally formed by the colon.

As illustrated above, controller 210 comprises a handle 42 defining an axial direction A to be handled by an operator, a rotatable bearing structure 44 connecting between handle 42 and the torsion shaft 30C and the outer elongated shaft structure 10 and is configured and operable to rotate the bending section about the axial direction A and a mode selector 48 capable of allowing the operator to rotate the bending section by rotating the handle 42 or by rotating the rotatable bearing structure 44. A mode selector 48 is capable of operating the endoscopic device in two operative modes: one locked mode being capable of blocking the rotatable bearing structure, and one unlocked mode capable of allowing the operator to rotate the bending section by rotating the rotatable bearing structure 44 about the axial direction A.

Figure 2B:
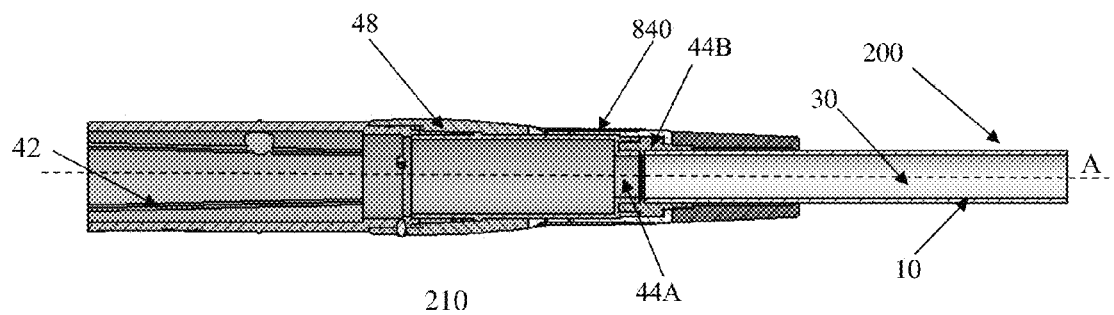
FIG. 2B schematically illustrates a partial view of another example of an orientation controller according to some embodiments of the present invention.

Reference is made to FIG. 2B illustrating an example of the configuration of an orientation controller 210, according to some embodiments of the present invention. The orientation controller 210 is configured to be connected to an insertion unit 200 of an endoscopic device having a rotatable and steering bending section. The insertion unit may be formed by a unit made of an elongated shaft as illustrated in FIG. 1. Controller 210 comprises a handle 42 to be handled by an operator, a rotatable bearing structure 44 being capable of rotating around itself (illustrated in the figure by two elements 44A and 44B) connecting between handle 42 and the insertion unit 200 and being configured and operable to rotate the bending section and a mode selector 48 having two operative modes: one locked mode being capable of allowing the operator to rotate the bending section by rotating the handle 42 and one unlocked mode capable of allowing the operator to rotate the bending section by rotating the rotatable bearing structure 44.

In some embodiments of the present invention, insertion unit 200 comprises an inner elongated shaft structure 30 surrounded by an outer elongated shaft structure 10. Inner elongated shaft structure 30 has thus a diameter smaller than outer elongated shaft structure 30. Moreover, the inner elongated shaft structure 30 and the outer elongated shaft structure 10 form together an integrated insertion unit 200 connecting at its extremities via a rotatable bearing structure 44 at one side of the orientation controller 210.

The inner elongated shaft 30 connected to the orientation controller 210 at one edge and to the bending section at the other, is able to transfer rotation of the orientation controller 210 directly to the distal tip through the insertion unit 200, without affecting the position of the insertion unit 200. In this configuration, rotatable bearing structure 44 comprises a inner rotatable bearing element 44A connecting between the inner elongated shaft structure 30 and the handle 42 and an outer rotatable bearing element 44B connected to the outer elongated shaft structure 10 such that the inner rotation bearing element 44A can rotate within the outer rotatable bearing element 44B.

In this configuration, orientation controller 210 is thus configured and operable to selectively connect the handle 42 to the inner elongated shaft structure 30 without the outer elongated shaft structure 10 or together with the outer elongated shaft structure 10. Orientation controller 210 is configured to allow free rotation in the two directions (clockwise or counterclockwise).

In some embodiments, mode selector 48 is capable of allowing the operator to decide if the rotation of the bending section (310 of FIG. 1) is made by moving the handle 42 (in a locked mode) or if the rotation of the bending section (310 of FIG. 1) is made by moving only the inner elongated shaft structure itself 30 (in an unlocked mode). In one operative locked mode in which the rotation is made by moving the handle 42, this may be implemented by blocking the rotatable bearing structure 44 such that the inner elongated shaft structure 30 together with the rotatable bearing structure 44 are free to move and rotate. In the second operative unlocked mode, in which the rotation is made by moving only the inner elongated shaft structure 30, the rotatable bearing structure 44 is released from the handle 14 such that the inner elongated shaft structure 30 is free to move alone and can rotate. For example, mode selector 48 may comprise an outer wheel 840. Upon activation of mode selector 48 (e.g. displacement towards the bending section) outer wheel 840 can be immobilized and cannot rotate, blocking the rotatable bearing structure 44 such that the inner elongated shaft structure 30 together with the rotatable bearing structure 44 and the handle 42 are free to move and rotate. Upon deactivation of mode selector 48 (e.g. displacement in the direction opposite to the bending section), outer wheel 840 can be released and can rotate, releasing the rotatable bearing structure 44 such that the inner elongated shaft structure 30 is free to move alone and rotate.

Figure 3A:
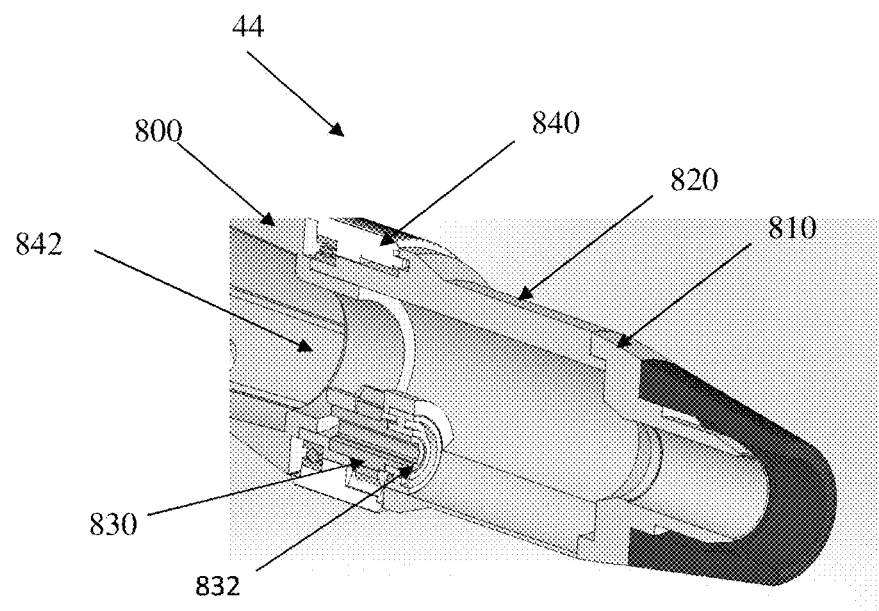
FIGS. 3A-3B schematically illustrate partial cross sectional views of an example of a rotatable bearing structure according to some embodiments of the present invention.

Reference is made to FIG. 3A illustrating an example of a rotatable bearing structure 44 incorporating a gear mechanism 800 according to some embodiments of the present invention. Gear mechanism 800 comprises an inner wheel 830 configured to hold an extremity of the inner elongated shaft structure (e.g. torsion shaft 30C of FIG. 2B) and an outer wheel 840 configured to rotate the inner wheel 830 while mode selector 48 is in unlocked mode. Activation (e.g. displacement) of the mode selector 48 to locked mode, blocks the outer wheel 840 which cannot rotate. Rotatable bearing structure 44 comprises an outer shaft holder 810 configured to hold an extremity of the outer elongated shaft structure. Gear mechanism 800 is configured to allow free rotation between the outer elongated shaft structure and the inner elongated shaft structure. Rotatable bearing structure 44 comprises inter alia an indentation 842 for accommodating the handle portion of the orientation controller, and a gear holder 820 configured for accommodating a plurality of channels running through the length of the insertion unit 200 from the handle straight to the outer elongated shaft structure. Inner wheel 830 is configured to move freely inside the gear holder 820 for example, due to an inner bearing 832 and by rotation of the outer wheel 840. The gear mechanism is configured and operable to transfer a small movement of rotation from the operator hand to a larger movement of the bending section, and therefore achieve more range and less delay.

Figure 3B:
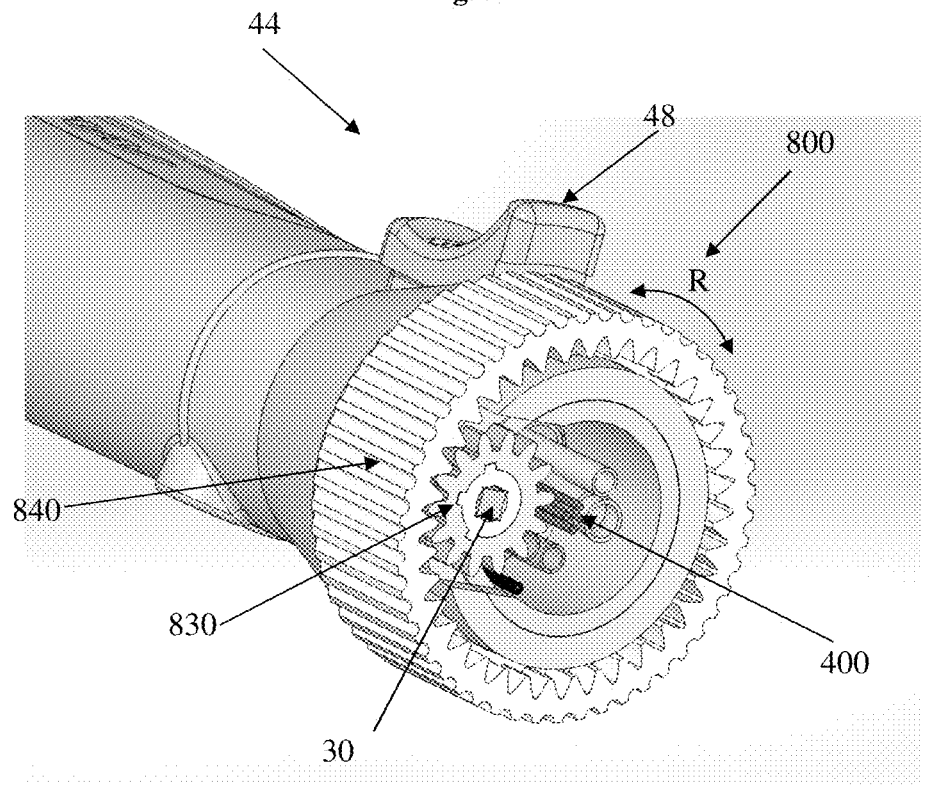

Reference is made to FIG. 3B illustrating another cross sectional view of the rotatable bearing structure 44 incorporating a gear mechanism 800 according to some embodiments of the present invention. Gear mechanism 800 comprises an inner wheel 830 configured to hold an extremity of the inner elongated shaft structure 30. The outer wheel is configured to block the rotation of the rotatable bearing structure 44 upon displacement of the mode selector 48. As described above, mode selector 48 is capable of allowing the operator to decide whether to use the gear mechanism 800 or not. This may be implemented by blocking, in one locked operative mode, in which the rotation is made by moving the handle, an outer wheel 840 of the gear mechanism 800 such that the outer wheel 800 is immobilized and cannot rotate. For example, displacement of the mode selector 48 blocks the outer wheel 800 which cannot rotate. In other words, in this mode, gear mechanism 800 is neutralized, the rotation of the orientation controller can rotate the distal tip in a ratio of 1:1 because the inner elongated shaft and the handle are moving together. In the second unlocked operative mode in which the gear mechanism 800 is used, the operator can rotate the outer wheel 840 in both rotational directions R. The rotation of the outer wheel 840 can rotate the bending section in the ratio of the gear. The mode selector 48 may be configured as a knob selectively operating the two locked and unlocked operative modes. The transmission ratio of the gear can be calculated from the diameter's wheels, as follows:

Gear's transmission ratio=outer wheel radius/inner wheel radius.

The figure shows the plurality of channels 400 running through the length of the insertion unit 200 from the handle straight to the outer elongated shaft structure.

Figure 4A:
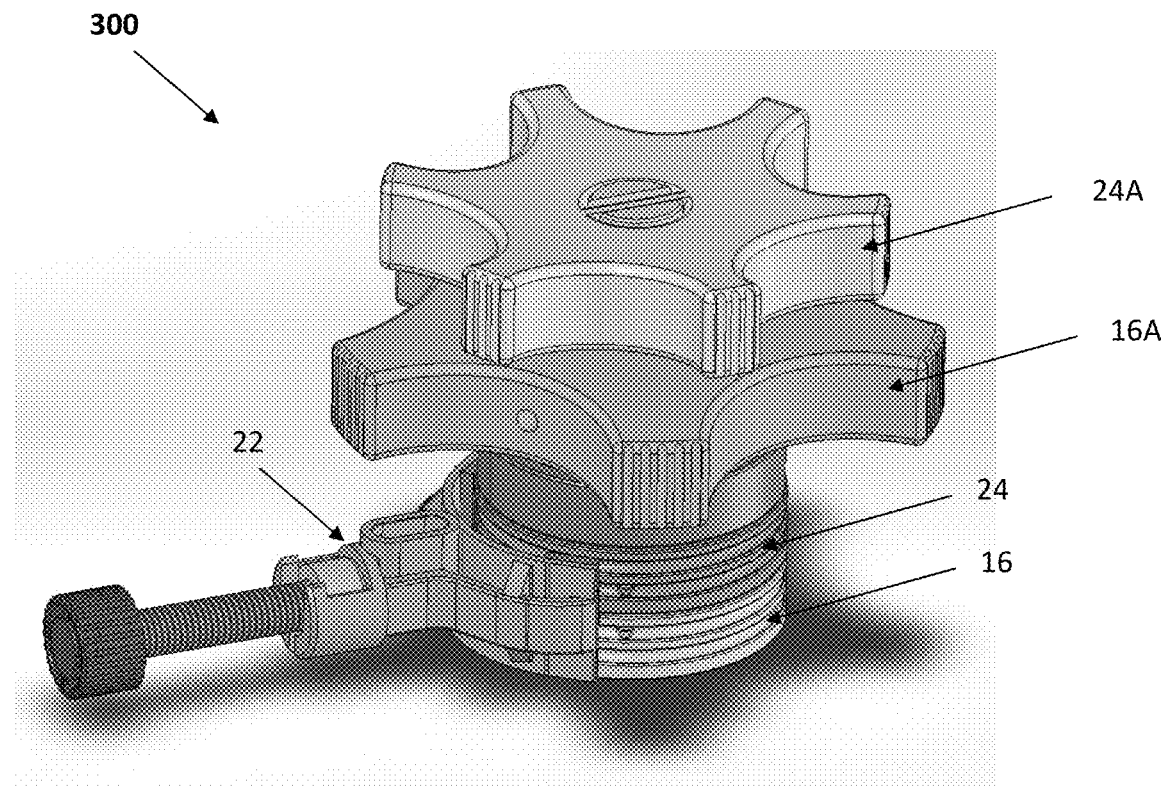
FIGS. 4A-4E show different views of examples of a mechanical steering mechanism according to some embodiments of the invention.

Reference is made to FIG. 4A, exemplifying a perspective view of a thread pulling device 300 such as mechanical knobs according to some embodiments of the present invention. In this configuration, the thread pulling device 300 comprises two pulleys 16 and 24 being operated by two controller wheels 16A and 24A respectively. The pulleys 16 and 24 are configured for separating the control of the steering, such that one pulley is configured and operable for directing the optical head leftwards and rightwards, while the second pulley is configured and operable for directing the optical head upwards and downwards. Pulley 16 is configured and operable for steering the optical head in the left and right directions, while pulley 24 is configured and operable for steering the optical head in the up and down directions. This novel configuration enables to provide full control of the steering device. The controller wheels 16A and 24A can be rotated clockwise and counterclockwise by the user in order to pull the steering threads. This action rotates the optical head to the desired direction. Each pulley holds two steering threads being configured for moving the optical head in opposite directions (i.e. left and right, or up and down). In this way, while one of the threads is being pulled, the other thread is released from tension. The pulleys 16 and 24 operate in the same manner, but for different directions.

In some embodiments, the thread pulling device 300 also comprises a locking mechanism 22, configured to lock the steering mechanism in the desired locked position. The pulleys 16 and 24 are thus configured for orienting the steering thread 14 at any desired position and tension, and, when the desired position is reached, locking mechanism 22 is configured for locking the steering mechanism at a specific steered position, locking the optical head at a specific position. The locking capability of the steering mechanism of the present invention enables to provide an accurate inspection of any desired region within the body lumen. The locking mechanism 22 locks the pulleys 16 and 24 but still allows a very fine movement of the controller wheels (e.g. knobs) 24A and 16A for a very fine steering for the removal of polyp stage. More specifically, locking mechanism 22 has two operative modes. In normal operation (e.g. free mode), the screw of the locking mechanism 22 does not come into contact with the pulleys 16 and 24. The screw is turned to lock the pulleys 16 and 24. The screw presses the pulleys 16 and 24, creates a friction force on the pulleys 16 and 24 and locks them to move. In order to rotate them and overcome the friction, a large force should be applied on the knobs 24A and 16A, providing a very fine movement of the controller wheels (e.g. knobs) 24A and 16A for a very fine steering for the removal of polyp stage. The operator may then decide whether to increase the resolution of the image of the specific region of interest, while the steering mechanism is locked in the optimal locked position.

Figure 4B:
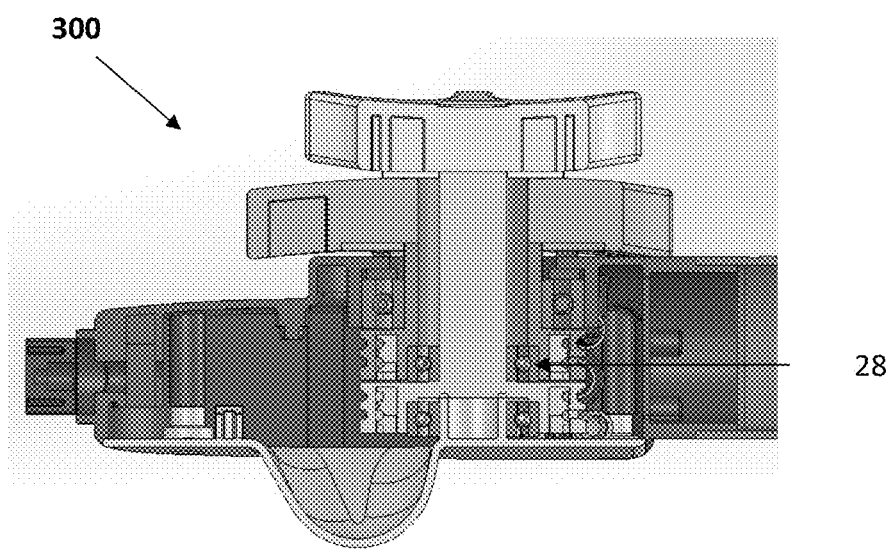

The pulleys 16 and 24 are connected to each other (e.g. by using bearings) in a way that each pulley can operate without affecting the other pulley. In this way, the thread pulling device 300 allows 360° optical head control. In this connection, reference is made to FIG. 4B exemplifying a cross-sectional view of the thread pulling device 300. Bearing 28 connects between the pulleys 16 and 24 to enable rotation of each pulley independently.

Figure 4C:
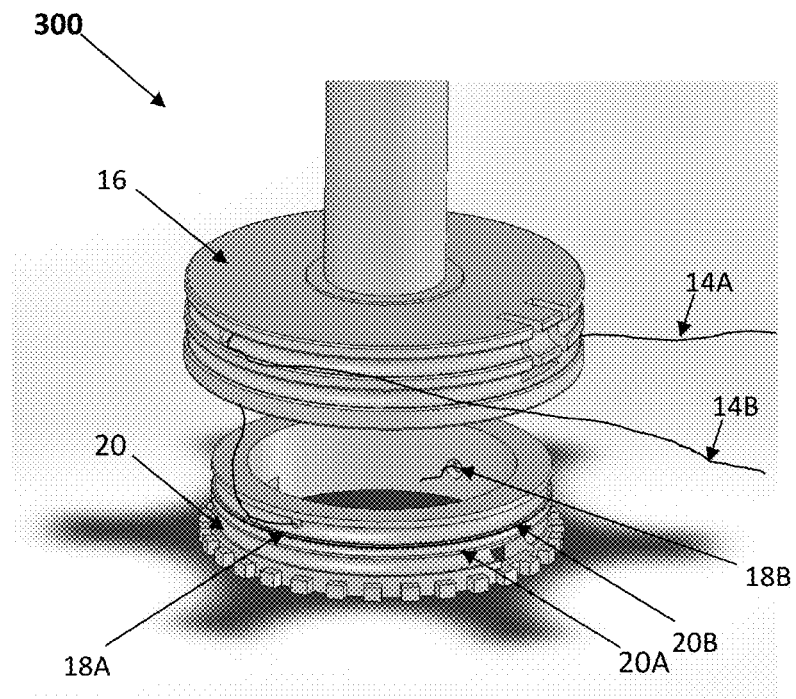

More specifically, as exemplified in FIG. 4C, one end/extremity of the non-metal steering threads 14A and 14B is threaded to fastening points 18A and 18B respectively, knotting the ends of the non-metal steering threads 14A and 14B to prevent threads 14A and 14B from becoming detached from the wheel 20. The fastening points 18A and 18B are configured as two openings in the tension wheel 20 through which the extremity of each steering thread passes through respectively. The extremity of the steering threads 14A and 14B are connected to a pulley 16 that is rotated to bend the bending section, and the steering threads 14A and 14B are enwrapped around the pulley 16. Each thread 14A and 14B is enwrapped a few loops around a respective slot 20A and 20B in the wheel 20. The threads 14A and 14B are threaded via two holes (not shown) located on the pulley 16. In order to lock the threads 14A and 14B, wheel 20 is inserted into pulley 16. As described above, each steering thread 14A and 14B, is enwrapped around its respective slot 20A and 20B by turning the tension wheel 20 within the pulley 16 using a motion controller 26 as exemplified in FIG. 4D below. The other extremity of the steering threads 14A and 14B is connected to one of an outermost spaced-apart element or the tube's distal end. This novel configuration in which the thread connection is implemented by wrapping the non-metal thread a few loops around the tension wheel 20 tightly and locking the steering threads 14A and 14B due to the insertion of wheel 20 into pulley 16 solves the problem mentioned above of fastening a non-metal thread to a pulley.

This novel configuration provides a basting of the steering thread around the pulley, fastening the steering thread to the pulley while allowing a fine movement of the controller wheels (e.g. knobs) 24A and 16A for a fine steering for the removal of polyp stage. In this connection, it should be noted that the thread cannot be fixed to the tension wheel by using an adhesive material, since the surface of the thread is too small to withstand shearing stress. For example, the diameter of the thread may be in the range of about 0.1-0.5 mm.

Moreover, this configuration provides an accurate tension on the thread, preventing slack of the thread that may be achieved by the teeth of the tension wheel. It should be understood that the more teeth the tension wheel 20 has around it, the more accurate the locking position of the wheel 20 within the pulley 16, thus facilitating better prevention of slack of the thread.

Figure 4D:
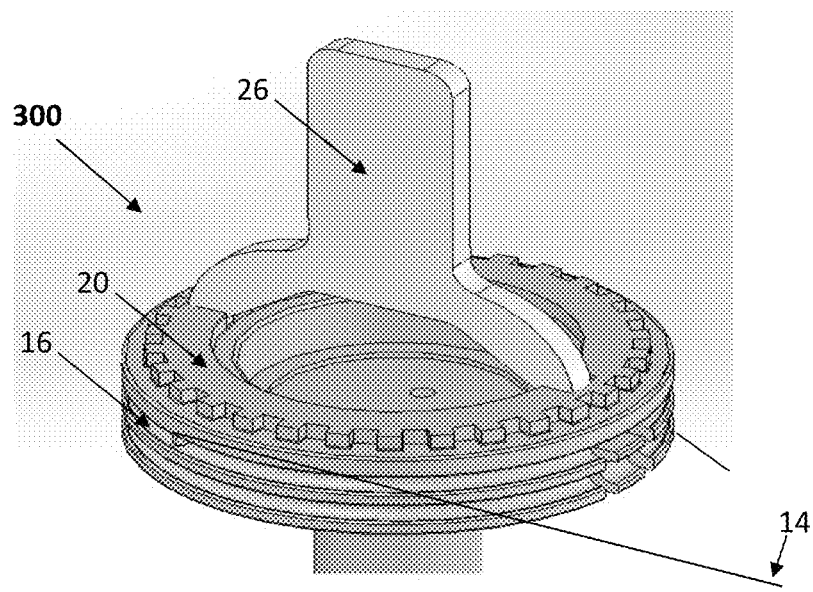

Reference is made to FIG. 4D exemplifying a partial view of the rear side of the thread pulling device 300 being in a locked position according to some embodiments of the present invention. In this specific and non-limiting example, the threaded wheel 20 is secured within the pulley 16 in a locked position upon activation of the operator of a motion controller 26 (e.g. jig). In the locked position, the tension wheel 20 is pushed towards the pulley 16 until the locking teeth of the threaded wheel 20 insert their final position. Engagement of the teeth of the wheel within the pulley prevents the tension wheel from rotating.

Figure 4E:
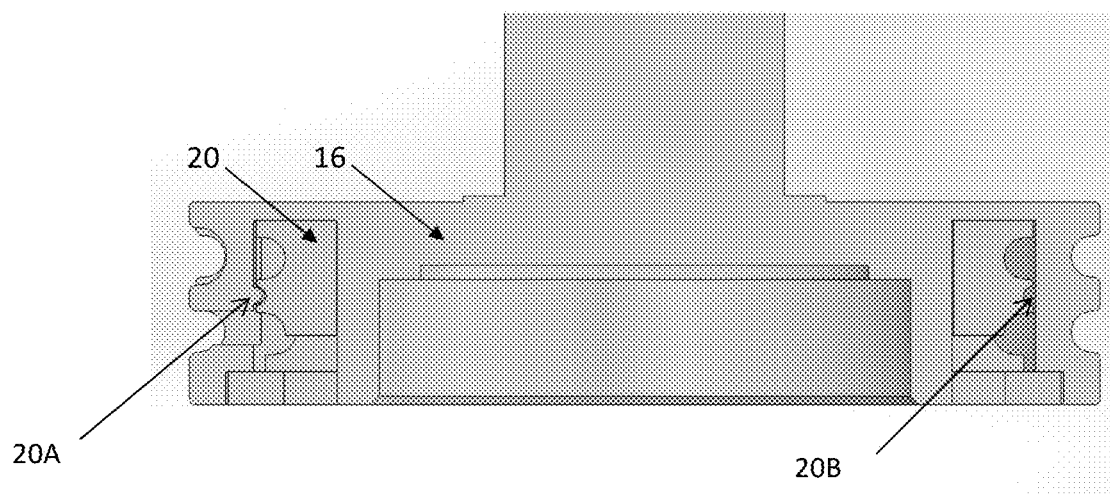

FIG. 4E exemplifies an enlarged cross-sectional view of the threaded wheel 20 engaged within the pulley 16 in a locked position. The threaded wheel 20 comprises two locking trenches 20A and 20B located at two opposite sides of the threaded wheel 20. In this novel configuration, the threaded wheel 20 has a first locking trench 20A configured as a fastener having groove-like configuration securing the threaded wheel 20 within the pulley 16 having snap-like configuration, and a second locking point 20B having the same configuration as 20A. The use of injection plastic elements, as described above, aimed at reducing the cost of the steering mechanism and rendering the steering mechanism disposable, enables the fastening of the elements, one to each other, by using snaps. This technique provides easy, simple, low-cost integration of locking parts for fastening tension wheel 20 into pulley 16.

Figure 5:
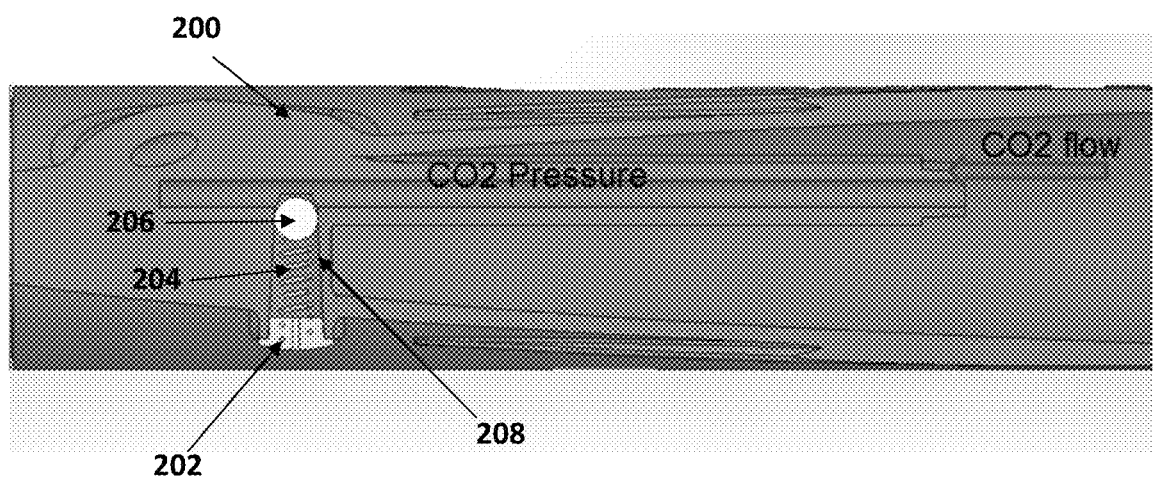
FIG. 5 shows an example of a release valve according to some embodiments of the invention.

Reference is made to FIG. 5, illustrating a release valve being configured to control the level of pressure exiting from a gas supply by releasing gas to the environment when the pressure reaches a certain threshold. Release valve 200 may be integrated within the handle of the endoscope and may be configured as a cavity 208 (e.g. valve housing) connected to a gas supply via a gas channel and is sealed at one end by a cover 202. Cover 202 is placed on top of a spring 204 on top of which a ball 206 is placed. Ball 206 is pressed against cavity 208 using spring 204 to seal the gas channel. The gas channel may be connected to cavity 208 via a tube (e.g. PVC) such that the pressure built up in the gas channel (i.e. the pressure in the colon) is also applied on a part of the ball surface. Whilst the force (Fpressure) acting on the ball 206 from the gas pressure remains lower than the force of the spring (Fspring) acting on the ball 206 from the spring 204, the valve is closed such that the GAS channel is sealed from the environment. If the pressure on the ball surface reaches a certain threshold and the force Fpressure acting on the ball 206 from the gas pressure becomes higher than the force Fspring acting on the ball 206 from the spring 204, a movement of the ball 206 towards valve cover 202 occurs, opening the valve and allowing venting of gas to the environment. The spring is selected to match the required release pressure.

The invention claimed is:

1. An orientation controller to be connected to an insertion unit of an endoscopic device having a rotatable bending section; said controller comprises:
   a handle defining an axial direction to be handled by an operator;
   a rotatable bearing structure connecting between the handle and the insertion unit;
   wherein said rotatable bearing structure is configured and operable to rotate the rotatable bending section of the insertion unit about the axial direction; and a mode selector capable of operating the endoscopic device in having a locked mode and unlocked operation modes, wherein operation of the locked operation mode blocks the rotatable bearing structure, and operation of the unlocked mode allows the operator to rotate the rotatable bending section by rotating the rotatable bearing structure about the axial direction;

wherein, when the insertion unit comprises an inner elongated shaft structure and an outer elongated shaft structure surrounding the inner elongated shaft structure; said rotatable bearing structure comprises an inner rotatable bearing element being configured for holding the inner elongated shaft structure, and an outer rotatable bearing element connected to the outer elongated shaft structure such that the inner rotation bearing element is capable of rotating within the outer rotatable bearing element, thereby rotating in the unlocked operation mode the rotatable bending section around itself without changing the outer elongated shaft structure's position inside the body lumen.

2. The orientation controller of claim 1, wherein in the unlocked mode in which the rotation is made by rotating the rotatable bearing structure, said mode selector is configured to release the rotatable bearing structure.

3. The orientation controller of claim 1, wherein said rotatable bearing structure comprises a gear mechanism, wherein said outer rotatable bearing element comprises an outer wheel configured to block rotation of rotatable bearing structure upon operation of said mode selector, and said inner rotatable bearing element comprises an inner wheel configured to be capable of free rotation by the outer wheel and to hold an extremity of the rotatable bending section, such that in a locked operation mode, rotation of the orientation controller rotates said inner elongated shaft structure inside said outer elongated shaft structure, and in an unlocked mode, rotation of the outer wheel rotates the inner elongated shaft structure via the inner wheel inside the outer elongated shaft structure.

4. The orientation controller of claim 3, wherein said gear mechanism is configured to allow free rotation between the outer elongated shaft structure and the inner elongated shaft structure; said gear mechanism further comprises an outer shaft holder configured to hold an extremity of the outer elongated shaft structure, wherein said inner wheel is configured to hold an extremity of the inner elongated shaft structure.

5. An intubation system comprising an insertion unit to be connected to a bending section of a medical instrument and an orientation controller as defined in claim 1.

6. The intubation system of claim 5, wherein said insertion unit comprises an inner elongated shaft structure being capable of torque transmission around its length axis and an outer elongated shaft structure surrounding the inner elongated shaft structure and having a continuous outer surface.

* * * * *